United States Patent
Begemann

(10) Patent No.: US 6,636,762 B2
(45) Date of Patent: Oct. 21, 2003

(54) METHOD AND SYSTEM FOR MONITORING HEART FAILURE USING RATE CHANGE DYNAMICS

(75) Inventor: Malcolm J. Begemann, CG Velp (NL)

(73) Assignee: Medtronic, Inc., Minneapolis, MN (US)

( * ) Notice: Subject to any disclaimer, the term of this patent is extended or adjusted under 35 U.S.C. 154(b) by 359 days.

(21) Appl. No.: 09/843,917

(22) Filed: Apr. 30, 2001

(65) Prior Publication Data

US 2002/0198462 A1 Dec. 26, 2002

(51) Int. Cl.[7] ............................................. A61B 5/0468
(52) U.S. Cl. ....................................................... 600/519
(58) Field of Search ................................. 600/516, 518, 600/519; 607/25

(56) References Cited

U.S. PATENT DOCUMENTS

| | | |
|---|---|---|
| 3,837,333 A | 9/1974 | Bruckeim |
| 4,316,472 A | 2/1982 | Mirowski et al. |
| 4,375,817 A | 3/1983 | Engle et al. |
| 4,379,459 A | 4/1983 | Stein |

(List continued on next page.)

FOREIGN PATENT DOCUMENTS

WO WO92/18198 10/1992

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

"Automatic Tachycardia Recognition" Arzbaecher et al, Pace, May–Jun., 1984, pp. 541–547.

PCT International Search Report, PCT/US/ 02/09895 (Oct. 28, 2002).

Primary Examiner—Jeffrey R. Jastrzab
(74) Attorney, Agent, or Firm—Thomas F. Woods; Eric R. Waldkoetter; Tom G. Berry

(57) ABSTRACT

A method of monitoring heart failure is provided. A baseline heart rate change value is determined, wherein the baseline heart rate change value comprises a speed at which a first initial heart rate changes to a second initial heart rate. At least one subsequent heart rate change value is also determined, wherein the subsequent heart rate change value comprises a subsequent speed at which a first subsequent heart rate changes to a second subsequent heart rate. The subsequent heart rate change value is compared to the baseline heart rate change value to obtain at least one heart failure value. Systems and programs for using the method are also provided.

60 Claims, 8 Drawing Sheets

U.S. PATENT DOCUMENTS

| | | |
|---|---|---|
| 4,384,585 A | 5/1983 | Zipes |
| 4,476,868 A | 10/1984 | Thompson et al. |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann et al. |
| 4,796,620 A | 1/1989 | Imran |
| 4,800,883 A | 1/1989 | Winstrom |
| 4,821,723 A | 4/1989 | Baker et al. |
| 4,862,361 A | 8/1989 | Gordon et al. |
| 4,880,005 A | 11/1989 | Pless et al. |
| 4,949,719 A | 8/1990 | Pless et al. |
| 4,953,551 A | 9/1990 | Mehra |
| 5,099,838 A | 3/1992 | Bardy |
| 5,117,824 A | 6/1992 | Keimel et al. |
| 5,131,388 A | 7/1992 | Pless |
| 5,148,812 A | 9/1992 | Verrier et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,265,617 A | 11/1993 | Verrier et al. |
| 5,269,298 A | 12/1993 | Adams et al. |
| 5,312,453 A | 5/1994 | Shelton et al. |
| 5,314,430 A | 5/1994 | Bordy |
| 5,330,507 A | 7/1994 | Schwartz |
| 5,331,966 A | 7/1994 | Bennett et al. |
| 5,354,316 A | 10/1994 | Keimel et al. |
| 5,437,285 A | 8/1995 | Verrier et al. |
| 5,545,186 A | 8/1996 | Olson |
| 5,560,370 A | 10/1996 | Verrier et al. |
| 5,690,686 A | 11/1997 | Min |
| 5,749,900 A | 5/1998 | Schroeppel et al. |
| 5,800,465 A | 9/1998 | Thompson et al. |
| 5,840,039 A * | 11/1998 | Heikkila ..................... 600/519 |
| 5,842,997 A | 12/1998 | Verrier et al. |
| 5,921,940 A | 7/1999 | Verrier et al. |
| 6,035,233 A | 3/2000 | Schroeppel et al. |
| 6,045,513 A | 4/2000 | Stone et al. |

* cited by examiner

METHOD AND SYSTEM FOR MONITORING HEART FAILURE USING RATE CHANGE DYNAMICS

FIELD OF THE INVENTION

The present invention relates to the field of medical monitoring devices. More particularly, the present invention relates to cardiac pacing systems that provide a method for monitoring heart failure based on the speed of rate changes in the hemodynamic performance of the heart.

BACKGROUND OF THE INVENTION

Heart failure is a disease that may be characterized by such symptoms as left ventricular dysfunction, arrhythmias, pulmonary and peripheral congestion, fatigue and shortness of breath. In earlier stages, patients may not be able to perform strenuous activities and, in later stages, may not even be able to perform routine activities such as climbing the stairs. Furthermore, the relationship between inability to perform strenuous activities and the corresponding state of the patient's heart may be difficult to discern and quantify.

Close monitoring of patients who experience heart failure or who are determined to be at risk for heart failure may be desirable. However, such monitoring presents some difficulties. For example, each patient's heart differs from that of another patient. One patient in earlier stages of heart failure may have a different activity profile than another, more physically fit patient, in the same stage of heart failure. Additionally, external methods of monitoring heart failure in a patient may be awkward. For example, a patient may seem to be in one stage of heart failure while being assessed at his physician's office while in fact, his actual everyday activities would indicate he is in a completely different stage of heart failure. Moreover, invasive methods of more closely examining a patient's stage of heart failure may not be desirable in all patients, such as those who are in reasonably early stages.

Some patients with a history of heart failure are treated with implantable pulse generators, such as pacemakers. Implantable pulse generators (IPGs) are well known in the art. As these IPGs are already implanted within the patient and providing cardiac data, it may be desirable to use such devices to determine the status of heart failure in such patients.

In particular, it may be desirable to monitor a heart failure patient in order to determine that his hemodynamic performance is sufficient under conditions of stress, such as exercise. The heart rate's response to such conditions depends on the hemodynamic performance of the heart. A pronounced increase in heart rate may well indicate low hemodynamic performance. That is, a heart rate that increases at a very high speed may indicate deteriorated pumping function, which in turn, may indicate, heart failure. However, the hemodynamic performance will be individual to each patient, particularly because other parameters, such as physical fitness, affect the speed at which heart rate changes.

Thus, a need exists in the medical arts for monitoring heart failure in a patient based on the speed at which the heart rate accelerates or decelerates in comparison to an individualized baseline value.

Some methods have been proposed in the prior art for measuring heart failure based on heart rate.

For example, U.S. Pat. Nos. 5,749,900 and 6,035,233 to Schroeppel et al. describe methods of measuring variability in heart rate and comparing the measured heart rate variability to a stored variability zone. Selective therapy regimes may be initiated depending on the heart rate variability measurement.

U.S. Pat. Nos. 5,148,812; 5,265,617; 5,437,285; 5,560,370; 5,842,997; 5,921,940 to Verrier, et al. describe methods of measuring cardiac vulnerability based on T-wave alternans analysis, simultaneous analysis of T-wave alternans and heart rate variability analysis, simultaneous assessment of autonomic function and cardiac electrical stability, simultaneous assessment of T-wave alternans and QT interval dispersion and assessment of physiological stress.

U.S. Pat. No. 6,045,513 to Stone et al. describes use of an IPG to monitor a patient's functional status.

U.S. Pat. No. 4,832,038 to Arai et al. describes use of power spectral analysis of heart rate to monitor cardiovascular regulation.

U.S. Pat. No. 4,862,361 to Gordon et al. also describes use of power spectral analysis of heart rate to monitor cardiovascular regulation.

The most pertinent prior art patents known are the present time are shown in the following table:

TABLE 1

Prior Art Patents

| Patent No. | Date | Inventor(s) |
|---|---|---|
| 5,749,900 | May 12, 1998 | Schroeppel et al. |
| 6,035,233 | Mar. 7, 2000 | Schroeppel et al. |
| 5,148,812 | Sep. 22, 1992 | Verrier et al. |
| 5,265,617 | Nov. 30, 1993 | Verrier et al. |
| 5,560,370 | Oct. 1, 1996 | Verrier et al. |
| 5,437,285 | Aug. 1, 1995 | Verrier et al. |
| 5,842,997 | Dec. 1, 1998 | Verrier et al. |
| 5,921,940 | Jul. 13, 1999 | Verrier et al. |
| 6,045,513 | Apr. 4, 2000 | Stone et al. |
| 4,862,361 | Aug. 29, 1989 | Gordon et al. |

The patents listed in Table 1 are hereby incorporated by reference herein, each in its entirety. As those of ordinary skill in the art will appreciate readily upon reading the Summary of the Invention, the Detailed Description of the Preferred Embodiments and the claims set forth below, at least some of the devices and methods disclosed in the patent of Table 1 may be modified advantageously in accordance with the teachings of the present invention.

SUMMARY OF THE INVENTION

The present invention is therefore directed to providing a method and system for monitoring heart failure based on the speed at which the patient's heart rate accelerates or decelerates compared to an individualized baseline value. The system of the present invention overcomes at least some of the problems, disadvantages and limitations of the prior art described above, and provides a more efficient and accurate means of monitoring heart failure in a patient.

The present invention has certain objects. That is, various embodiments of the present invention provide solutions to one or more problems existing in the prior art respecting the pacing of cardiac tissue. Those problems include, without limitation: (a) difficulty in monitoring the functional status of heart failure patients; (b) individual variation in the hemodynamic performance of different patients with heart failure; (c) difficulty in obtaining an indication of heart failure as patient's physical fitness changes; and (d) difficulty in determining an appropriate indication of heart failure for a particular patient.

In comparison to known pacing techniques, various embodiments of the present invention provide one or more of the following advantages: (a) monitoring heart failure in a patient based on the speed at which heart rate changes; (b) ability to obtain an indication of heart failure that is unique to each patient (c) ability to determine a baseline value for monitoring heart failure, and (d) ability to monitor trends over time in a heart failure patient.

Some embodiments of the present invention include one or more of the following features: (a) an IPG capable of monitoring heart failure in a patient; (b) an IPG capable of measuring rate dynamics in a patient; (c) methods of monitoring heart failure in a patient based on the speed at which the heart rate changes; (d) methods of setting individualized baseline values for monitoring the hemodynamic performance of a particular patient.

At least some embodiments of the present invention involve determining a baseline heart rate change value which reflects the speed at which a first initial heart rate changes to a second initial heart rate. At least one subsequent heart rate change value is determined which reflects the speed at which a first subsequent heart rate changes to a second subsequent heart rate. The subsequent heart rate change value may be compared to the baseline heart rate change to obtain at least one heart failure value. Several subsequent heart rates may be measured and several subsequent heart rate change values may be calculated. Two immediately subsequent heart rates may be compared to each other to achieve a subsequent heart rate change value. Alternatively, a given heart rate may be compared to any previous heart rate to determine a subsequent heart rate change values. Average, maximum, minimum heart rate change values may be determined for a given patient and stored or evaluated over time.

BRIEF DESCRIPTION OF THE DRAWINGS

The above, and other objects, advantages and features of the present invention will be more readily understood from the following detailed description of the preferred embodiments when considered in conjunction with the drawings, in which like reference numerals indicate identical structures throughout the several views, and wherein.

DETAILED DESCRIPTION OF THE PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
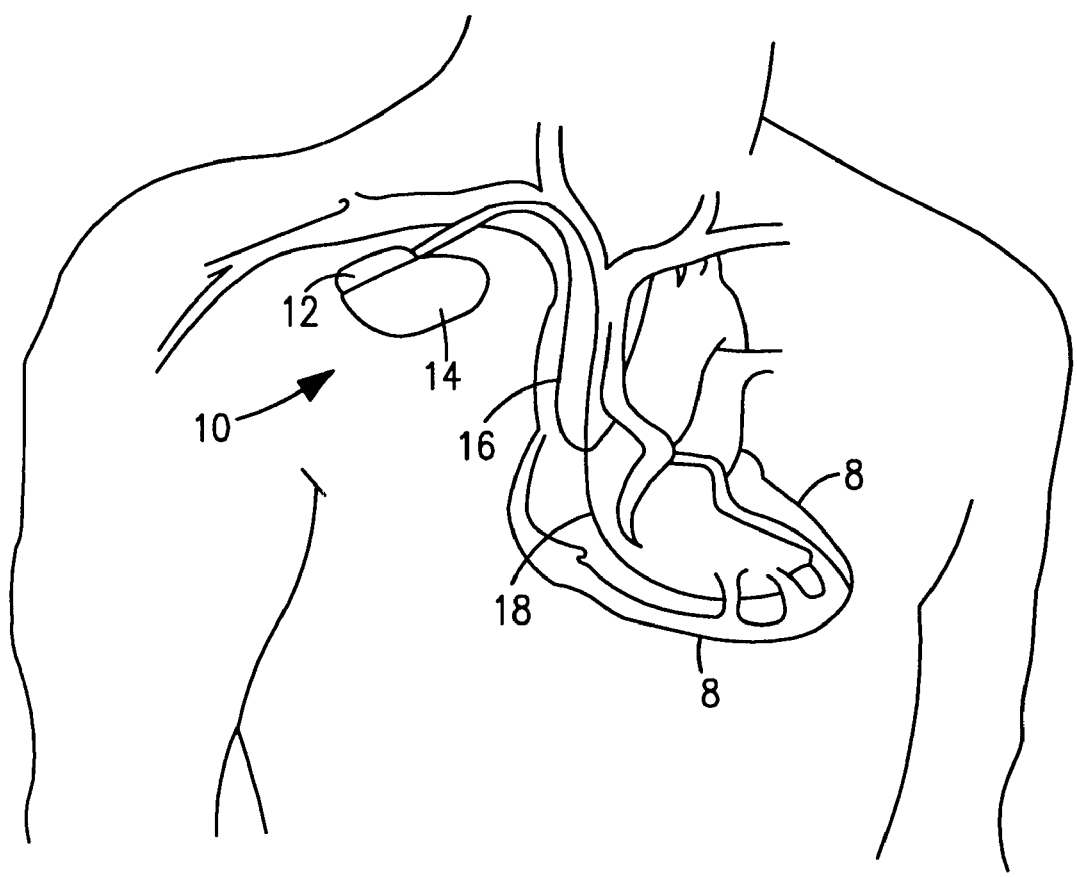
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference herein, each in its respective entirety.

Figure 2:
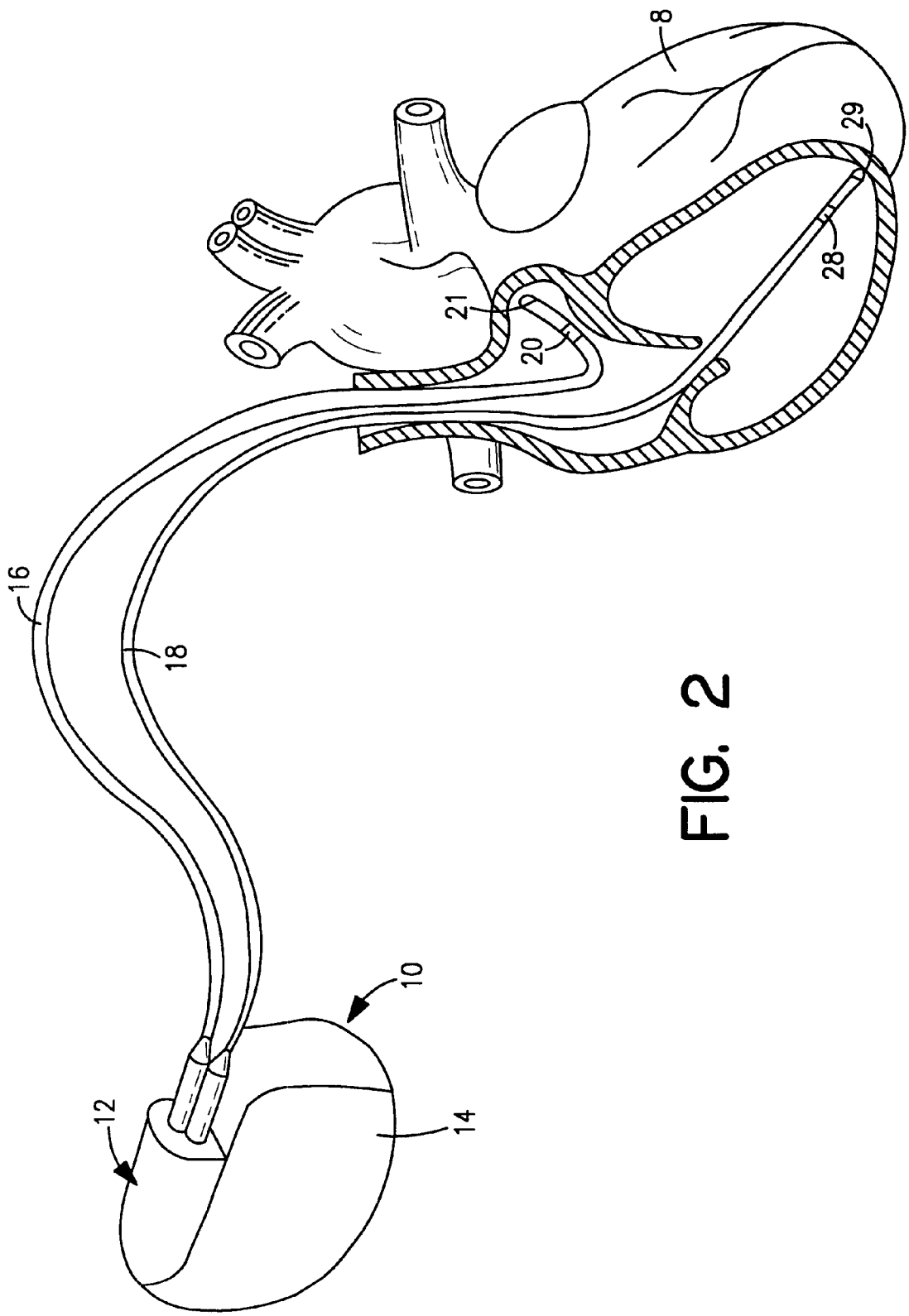
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
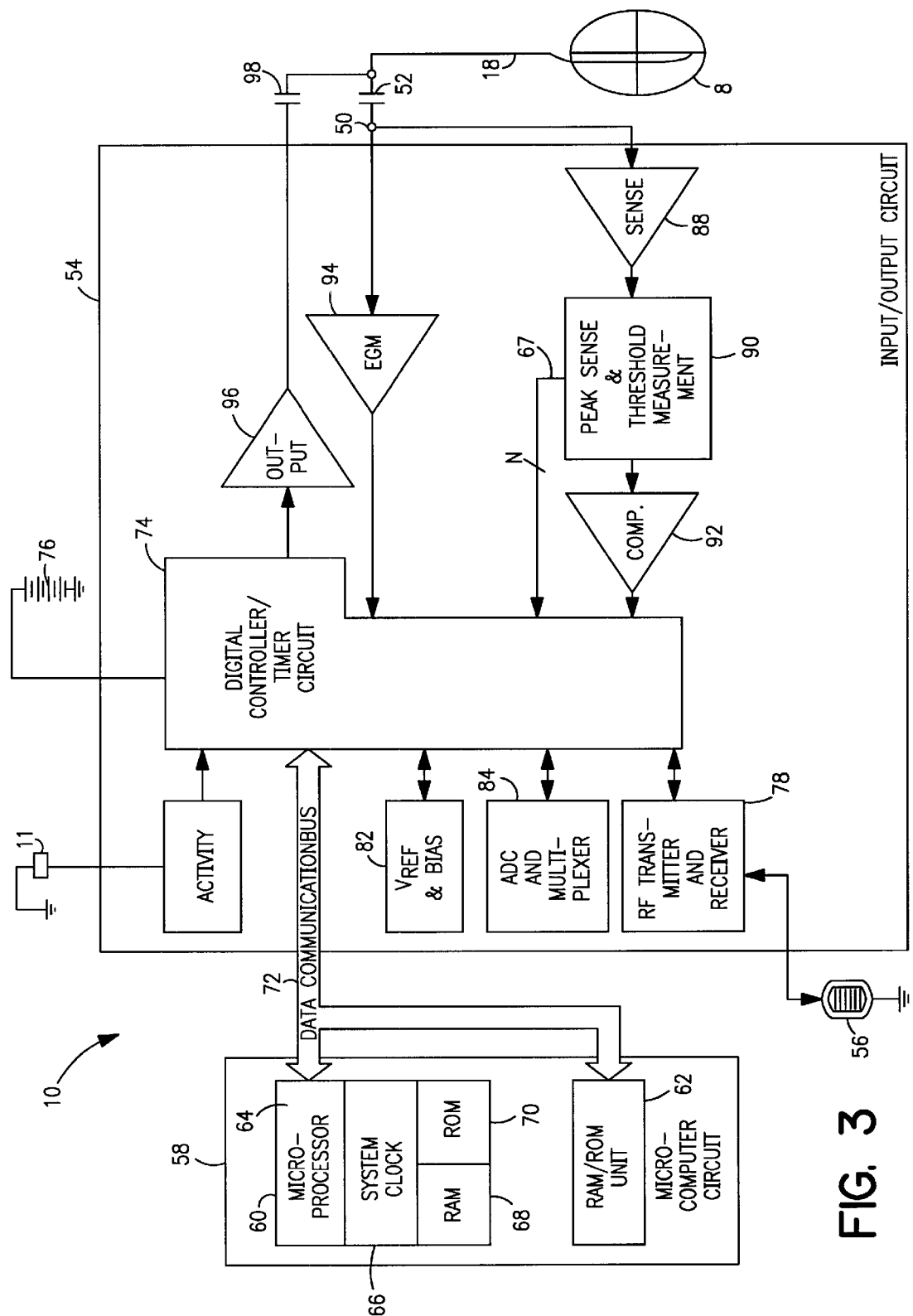
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which may be an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 may be programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Shelton et al., hereby incorporated by reference herein in its entirety. The programming methodology disclosed in U.S. Pat. No. 5,312,453 to Shelton et al. is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 may be attached to a hybrid circuit located inside hermetically sealed enclosure 14 of IMD 10. The output signal provided by activity sensor 11 is coupled to input/ output circuit 54. Input/output circuit 54 contains analog circuits for interfacing to heart 8, activity sensor 11, antenna 56 and circuits for the application of stimulating pulses to heart 8. Accordingly, the rate at which heart 8 is stimulated or beats spontaneously without stimulation may be controlled and/or monitored using software-implemented algorithms or pacing rate functions stored in microcomputer circuit 58.

Microcomputer circuit 58 may comprise on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 may include microprocessor 64, system clock circuit 66 and on-board RAM 68 and ROM 70. Off-board circuit 62 may comprise a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al., hereby incorporated by reference herein in its entirety, or to that disclosed in the above-referenced '453 patent to Shelton et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 may generate stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 may be coupled to sensing circuitry, including sense amplifier 88, peak sense and threshold measurement unit 90 and comparator/threshold detector 92. Circuit 74 may further be coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and WT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference herein, each in its respective entirety.

Figure 4:
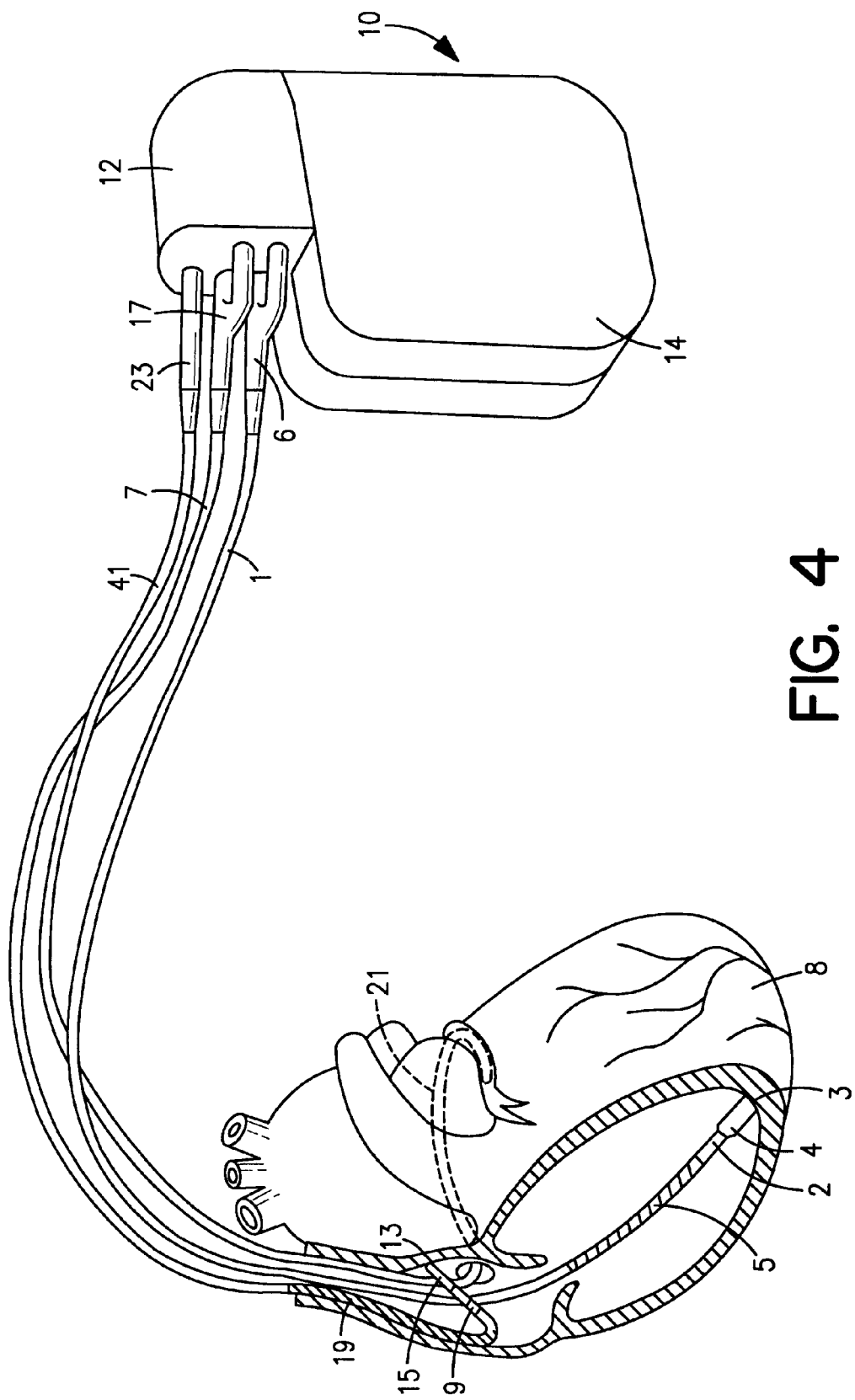
FIG. 4 is a schematic view of another embodiment of an implantable medical device, made in accordance with the present invention.
Figure 5:
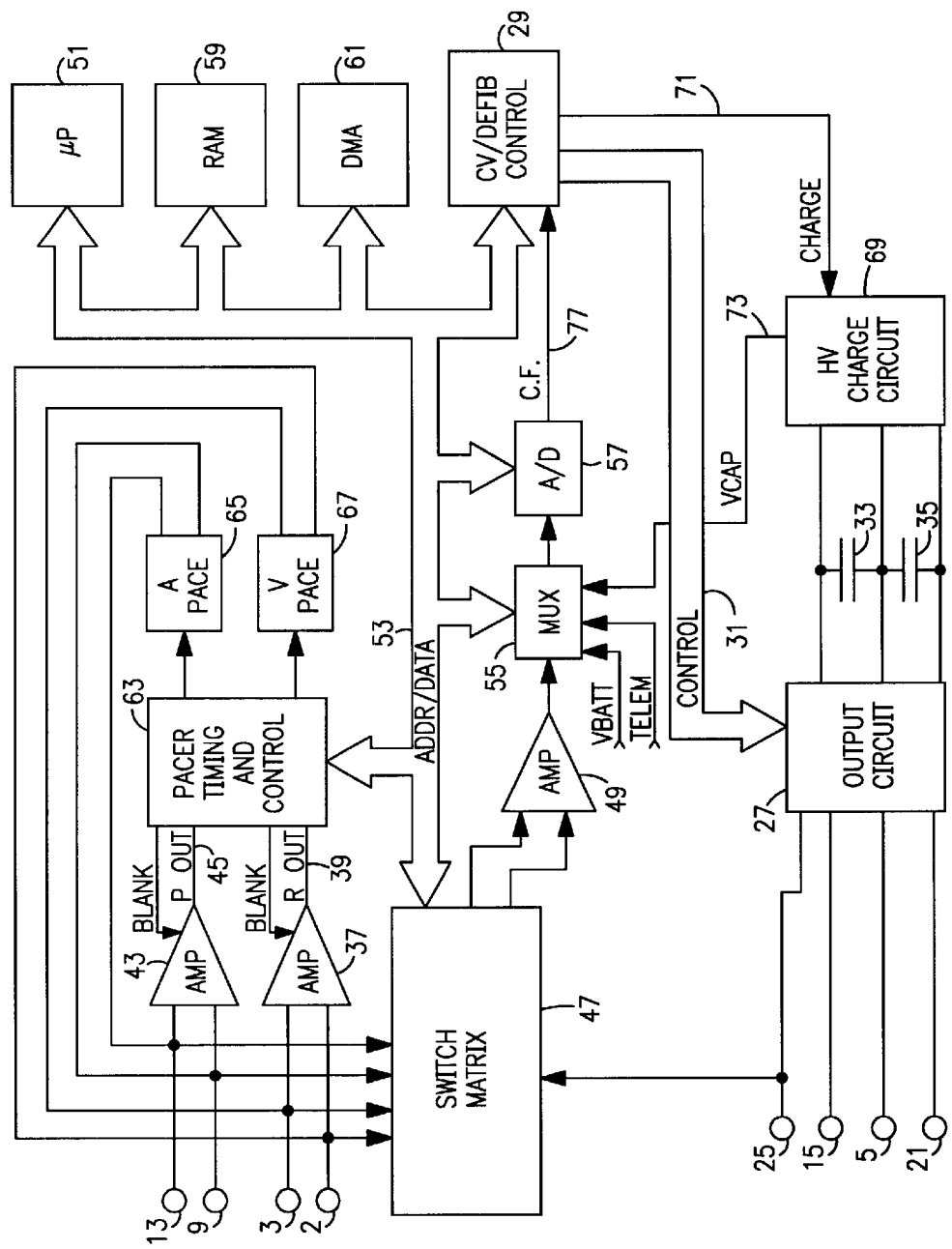
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 may be employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 may be employed for atrial pacing and for sensing atrial depolarizations. Elongated coil electrode 19 is provided proximal to electrode 9 and coupled to the third conductor within lead body 7. In one embodiment of the invention, electrode 19 is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which may take the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which may also take the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 may include programmable digital counters which control the basic time intervals associated with DDD, VVI, DVI, VDD, AAI, MIR, DDI and other modes of single and dual chamber pacing well known to the art. Circuitry 63 also may control escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 may operate as an interrupt driven device, and may be responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10,1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference herein, each in its respective entirety.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated herein by reference, each in its respective entirety, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference herein, each in its respective entirety, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference herein in its entirety.

An example of circuitry that may be used to control delivery of monophasic pulses is disclosed in U.S. Pat. No. 5,163,427 to Keimel, also hereby incorporated by reference herein in its entirety. Output control circuitry similar to that disclosed in U.S. Pat. No. 4,953,551 to Mehra et al. or U.S. Pat. No. 4,800,883 to Winstrom, both incorporated by reference, each in its respective entirety, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
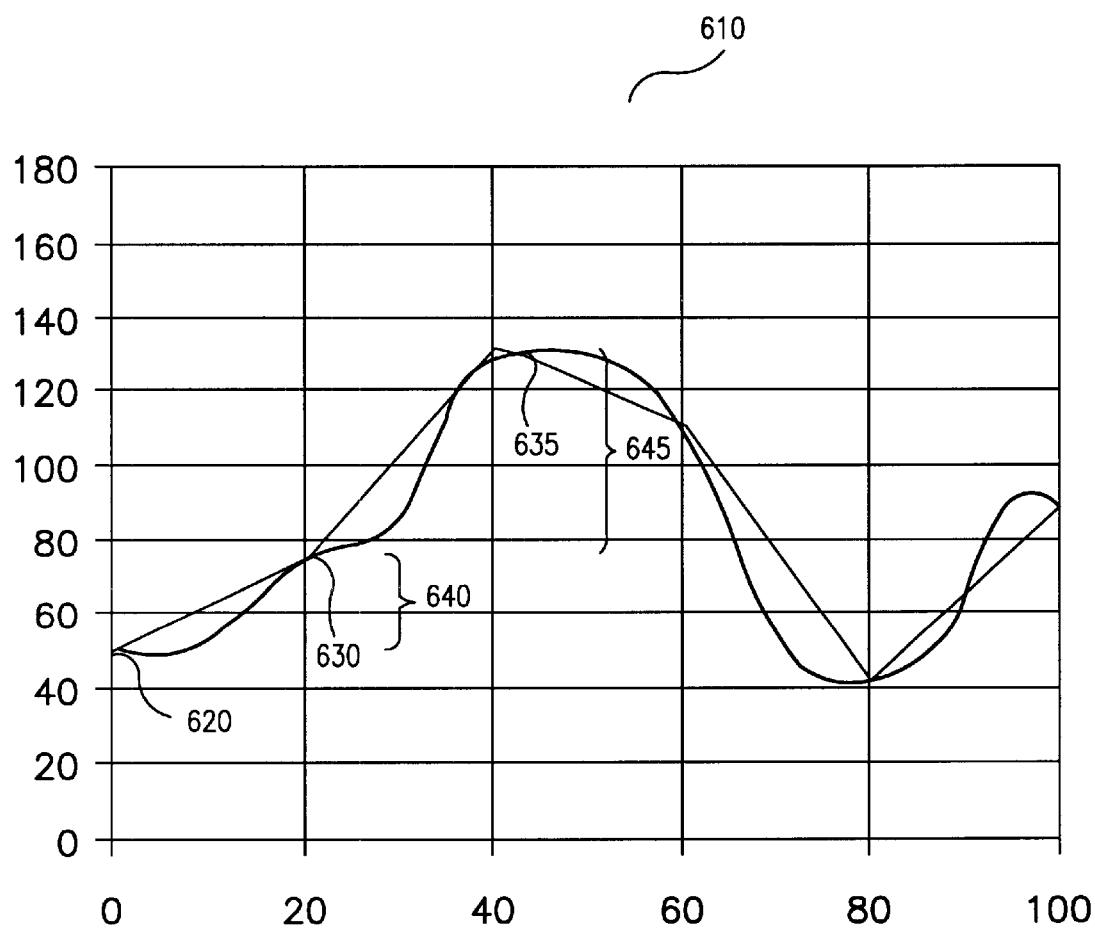
FIG. 6 is a graph illustrating one embodiment of heart rate changes being evaluated in accordance with the presenting invention.

FIG. 6 shows a graph illustrating the operation of one embodiment of the present invention, where a baseline change in heart rate monitored by IMD 10 is compared to a subsequent change in heart rate, at 600. In one embodiment of the present invention, a subsequent change in heart rate which is significantly higher.

Time period 600 is the period of time over which at least two heart rate changes of heart 8 are monitored and compared. Any number of heart rate changes may be monitored and compared in accordance with the present invention. Time period 600 shown in FIG. 6 is 100 minutes, but also may range, without limitation, between 10 minutes to 10 days, over one or several weeks and over one or several months. In one embodiment of the invention, time period 600 may be a short-term time period such as one week and may be later compared with a different longer time period such as one month.

For example, in one embodiment of the invention, the heart rate is measured at fixed time intervals during time period 600. Thus, measurements may be taken, for example, at intervals ranging, without limitation, from every ten seconds, every twenty seconds, every thirty seconds or every 100 seconds. Alternatively, the measurements may be taken for example, at intervals ranging, without limitation, from every 5 minutes, every ten minutes, every 20 minutes, etc. Additionally, more than one timing interval could be taken (including, without limitation, every 10, 20, 30 and 60 seconds or every 10, 20, 30 and 60 minutes). In one embodiment of the invention, different measurements may be taken by sampling every x seconds with the resulting heart rate-change being a value calculated by subtracting every subsequent sample from the previous one i.e., heart rate change = current heart rate value ($n$) − previous heart rate value ($n-1$)

where n represents a sample number.

Alternatively, different measurements may be taken by sampling every x seconds with the resulting heart rate-change being a value calculated by subtracting every subsequent sample from a sample that is y samples ago.

i.e., heart rate change = current heart rate value ($n$) − earlier heart rate value ($n-y$)

Thus, the heart rate change may be calculated by subtracting sets of two subsequent heart rates.

For example, in FIG. 6, one heart rate value is measured at 620 and a subsequent value is measured at 630 and a third is measured at 635. The heart rate change value may then be determined by subtracting the value of the measurement taken at 620 from the value taken at 630. In FIG. 6, this calculation is that the heart rate change value equals 80 minus 50, giving a heart rate change value of 30. The next heart rate change value may then be determined by subtracting the value of the measurement taken at 630 from the value taken at 635. In FIG. 6, this calculation is that the heart rate change value equals 130 minus 80, giving a heart rate change value of 50. Alternatively, the next heart rate change value may be determined by subtracting the value of the measurement taken at 620 from the value taken at 635. In FIG. 6, this calculation is that the heart rate change value equals 130 minus 50, giving a heart rate change value of 80.

The resulting heart rate-change values may then be used to adapt and/or update stored heart rate-change values, such as, for example, average heart rate-change, maximum heart-rate change, and minimum heart-rate change (both positive and negative changes). These updated values are subsequently stored in specific time slots, resulting in an overview of these values over time, with each time slot having its own stored values (average, maximum, minimum etc.)

Thus for time period 600, an average heart rate change may be calculated by adding all the calculated heart rate change values and calculating an average change. In FIG. 6, the heart rate change values are 30, 50 and 80 resulting in an average heart rate change of 53. This value may be stored as an average heart rate change for a given patient for example at a storage location of IMD 10, including but not limited to, a location of memory 59, RAM 68 or ROM 70.

Also for time period 600, a maximum heart rate change may be determined by discerning the maximum heart rate value from all the gathered heart rate change values. In FIG. 6, the heart rate change values are 30, 50 and 80 so the maximum value is 80. This value may be stored as a maximum heart rate change for a given patient for example at a storage location of IMD 10, including but not limited to, a location of memory 59, RAM 68 or ROM 70.

Also for time period 600, a minimum heart rate change may be determined by discerning the minimum heart rate value from all the gathered heart rate change values. In FIG. 6, the heart rate change values are 30, 50 and 80 so the minimum value is 30. This value may be stored as a minimum heart rate change for a given patient for example at a storage location of IMD 10, including but not limited to, a location of memory 59, RAM 68 or ROM 70.

Heart rate-change measurements over a short time period 600 may provide information about the short term adaptation of heart 8 to conditions of stress such as exercise. Meanwhile, heart rate-change measurements taken over longer time periods 600 may provide information about the long-term adaptation of heart 8 to conditions of stress such as exercise. Furthermore, multiple time interval measurements may be combined or compiled to provide additional information (e.g., short term measurements correlated to longer term measurements may provide further information about the average adaptation of heart 8 to conditions of stress.)

For example, the changes over time in one individual may be examined using information gathered in accordance with the present invention. This can be done by taking a long term average (e.g. an average of values over 6 months, over 6 weeks, over 24 hours or over another such long time period 600) and comparing that with a shorter term average (e.g. an average of values over last month, over last week, over the last hour, over another such shorter time period 600).

In FIG. 6, function 610 indicates changes in the heart rate of heart 8. In one embodiment of the invention, IMD 10 paces heart 8 and also is adapted to monitor heart rate changes in heart 8 in accordance with the present invention. Thus, function 610 may also include provisions for predetermining, setting and/or implementing a lower rate limit function (i.e., the lowest rate at which a patient's heart is permitted to be paced and/or monitored), an upper rate limit function (i.e., the highest rate at which a patient's heart is permitted to be paced and/or monitored), or both lower and upper rate limit functions (i.e., function 610 may comprise both upper and lower rate limit functions).

Preferred lower rate limits suitable for use in the present invention range between about 25 beats per minute (bpm) and about 75 beats ppm, more preferably range between about 30 bpm and about 70 bpm, more preferably yet range between about 35 bpm and about 65 bpm, and most preferably range between about 50 bpm and about 65 bpm. Preferred upper rate limits suitable for use in the present invention range between about 30 beats per minute (bpm) and about 120 beats ppm, more preferably range between about 50 bpm and about 120 bpm, more preferably yet range between about 70 bpm and about 120 bpm, and most preferably range between about 90 bpm and about 120 bpm.

Alternatively, function 610 may be a heart rate based on rates at which heart 8 beats when no electrical stimulation is provided thereto (i.e., the unpaced heart rate).

In the embodiment shown in FIG. 6, line 610 represents a changing heart rate change in the hemodynamic performance of heart 8. At the point indicated by 620, the initial heart rate of the heart is measured. The initial heart rate sensed by IMD 10 to calculate heart rate change in accordance with the present invention may be, for example, a pacing rate determined initially by the settings of the software-implemented algorithms associated therewith, may be determined on the basis of data gathered or acquired by IMD 10, may be preprogrammed, or may be set by the attending physician. In the embodiment of FIG. 6, the initial heart rate is 50 bpm but may range, for example between about 25 beats per minute (bpm) and about 75 bpm.

At the point indicated by 630, the heart rate of the heart 8 is measured a second time. In one embodiment of the invention, the value at 630 is measured after the heart has undergone a condition of stress, such as, for example, exercise. In one embodiment of the invention, the second measurement of initial heart rate is made automatically, for example, by sensing circuitry of IMD 10. The second measurement may be data gathered or acquired by IMD 10, such as data collected by sensing leads 16, 18 described above. Alternatively, the second measurement may be taken by the attending physician. In the embodiment of FIG. 6, the second measurement of initial heart rate is 80 bmp but may range, for example, between about 25 beats per minute (bpm) and about 75 bpm.

The change between points 620 and 630 and the corresponding change in heart rate may be determined. For example, difference 640 indicates the change over time between points 620 and 630. In the embodiment shown in FIG. 6, this change is a value of 30 bpm over 20 minutes or a 1.5 rate change value. The change over time may be linear, non-linear, step-wise, asymptotic, logarithmic, exponential and/or geometric in fashion, or in any suitable combination or permutation of the foregoing.

It is important to note that FIG. 6 illustrates merely one embodiment of the present invention, and is not intended the limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

As seen in FIG. 6, baseline heart rate values 620, 630 and baseline heart rate change 640 may also be predetermined and stored in a memory of microcomputer 58, set by the attending physician, determined on the basis of diagnostic data gathered or sensed by IMD 10 and stored in a memory thereof, external diagnostic means or a physician, or determined by comparison to a database or look-up table comprising singular values or ranges of values that have been determined to be acceptable and that are stored in microcomputer 58.

Additionally, IMD 10 and microcomputer 58 may be configured to update and change any of the baseline heart rate values 620, 630 and/or baseline heart rate change value 640 in response to detected changes in the physiological status of the patient, sensed cardiac or other physiological events occurring in the patient's body, changes made by an attending physician, changing environmental conditions, and so on. Thus, under the control of microcomputer 58 baseline heart rate change value may be changed as required or appropriate.

At the point indicated by 635, another measurement is taken of the heart rate. The heart rate sensed by IMD 10 to calculate heart rate change in accordance with the present invention may be, for example, a pacing rate determined initially by the settings of the software-implemented algorithms associated therewith, may be determined on the basis of data gathered or acquired by IMD 10, may be preprogrammed, or may be set by the attending physician. The heart rate sensed by IMD 10 may also be a heart rate at which heart 8 beats when no electrical stimulation is provided thereto (i.e., the unpaced heart rate). The heart rate may be sensed as a signal, such as an ECG signal, for example by IMD 10.

In the embodiment of FIG. 6, the heart rate is 130 bpm but may range, for example between about 25 beats per minute (bpm) and about 90 bpm.

The change between points 630 and 635 and the corresponding change in heart rate may be determined. For example, line 645 indicates the change over time between points 630 and 635. In the embodiment shown in FIG. 6, this change is a value of 50 bpm over 20 minutes or a 2.5 rate change value. The change over time may be linear, non-linear, step-wise, asymptotic, logarithmic, exponential and/or geometric in fashion, or in any suitable combination or permutation of the foregoing. Alternatively, the change between points 620 and 635 and the corresponding heart rate may be determined. In the embodiment shown in FIG. 6, this change is a value of 80 bmp over 40 minutes or a 2.0 rate change value.

As seen in FIG. 6, heart rate values 630, 635 and heart rate change 645 may also be predetermined and stored in a memory of microcomputer 58, set by the attending physician, determined on the basis of diagnostic data gathered or sensed by IMD 10 and stored in a memory thereof, external diagnostic means or a physician, or determined by comparison to a database or look-up table comprising singular values or ranges of values that have been determined to be acceptable and that are stored in microcomputer 58.

Additionally, IMD 10 and microcomputer 58 may be configured to update and change any of the heart rate values 630, 635 and/or baseline heart rate change value 645 in response to detected changes in the physiological status of the patient, sensed cardiac or other physiological events occurring in the patient's body, changes made by an attending physician, changing environmental conditions, and so on. Thus, under the control of microcomputer 58 baseline heart rate change value may be updated as required or appropriate.

In one embodiment of the invention, a marked difference between the baseline heart rate change 640 and another heart rate change 645 may indicate heart failure. If the pump function of heart 8 is deteriorated, the heart rate change from one heart rate measurement to another (e.g., from measurement 630 to 635) will initially be more pronounced than the heart rate change between baseline heart rate measurements (e.g., from measurement 620 to 630). In one embodiment of the invention, baseline heart rate change 640 is a normal heart rate change for a given individual. Baseline heart rate change 640 and baseline values 620, 630 may change over time for a given individual based on parameters including, but not limited to, physical fitness of the patient. Thus, these values may be updated as indicated above. These values may also be stored as indicated above, for example, to show trends over time.

Figure 7:
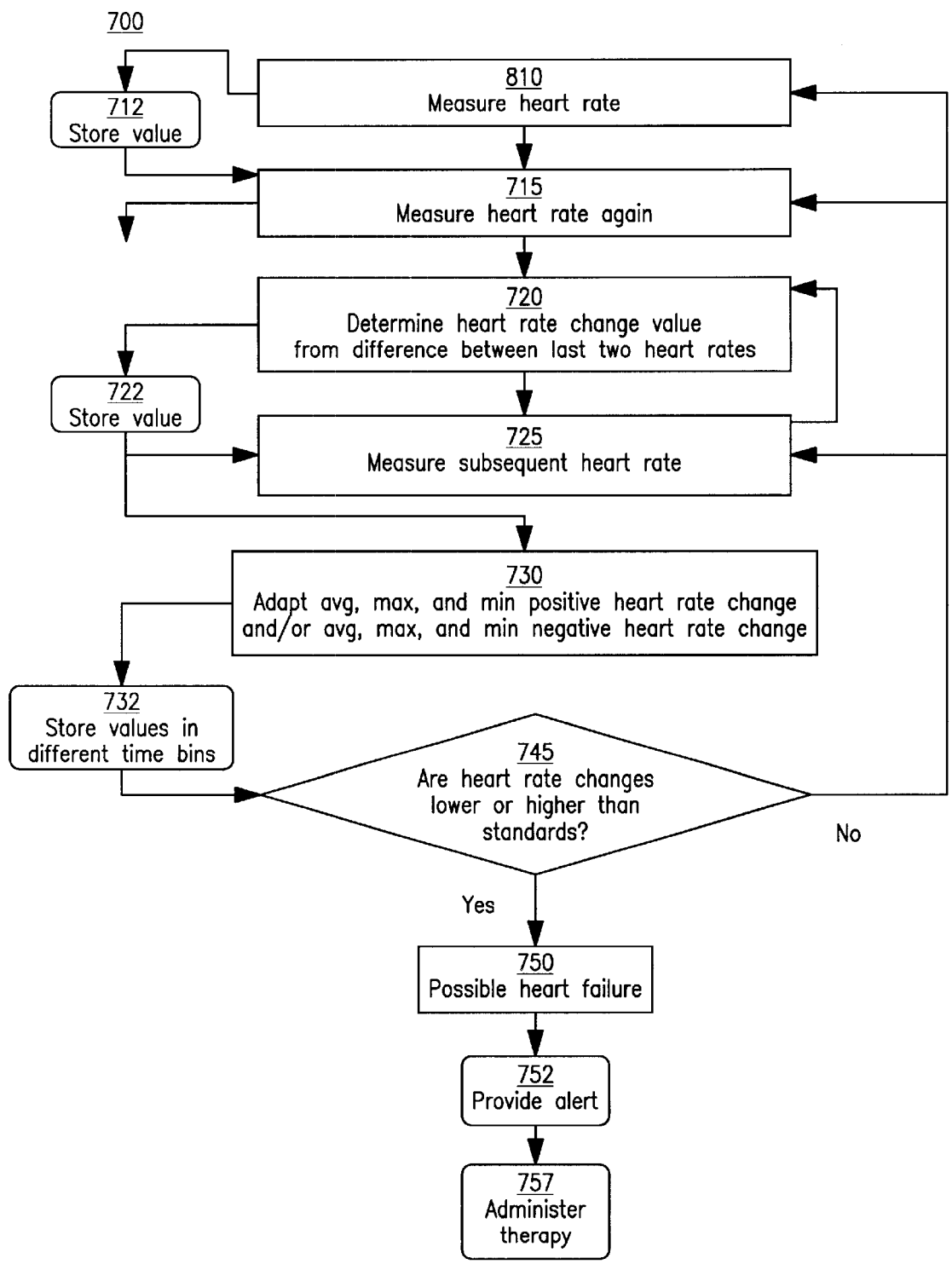
FIG. 7 is a flow diagram of one embodiment of a method for monitoring heart rate changes in accordance with the present invention.

FIG. 7 illustrates one embodiment of a method for monitoring a human heart in accordance with the teachings of the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

At block 710 a measurement of initial heart rate 620 is determined in accordance with one or more of the methods of determining same described above. Alternatively, initial heart rate 620 may be set by a physician, selected from a look-up table or database, or calculated.

At block 715, another initial heart rate measurement is taken after a predetermined time. This predetermined time may be a time set or selected automatically by a physician. The time may range anywhere between the entirety of time period 600 and some portion or fraction thereof. The heart rate measurement may also be taken after certain predetermined conditions are met, for example, after stress to the heart or after exercise.

At block 720, a baseline heart rate change 610 is determined. This heart rate change may be, for example, the change in heart rate from the first measurement of initial heart rate to the second measurement of initial heart rate. The heart rate change value may be expressed in any suitable manner, for example, as a function over time, e.g., a 25 bpm change over 40 minutes, as a constant, e.g. a 0.625 heart rate change value, or as a percentage, a 62.5% change in heart rate. In one embodiment of the invention, different measurements may be taken by sampling every x seconds with the resulting heart rate-change being a value calculated by subtracting every subsequent sample from the previous one i.e., heart rate change = current heart rate value (*n*) − previous heart rate value (*n* − 1)

where n represents a sample number.

Alternatively, different measurements may be taken by sampling every x seconds with the resulting heart rate-change with the resulting heart rate-change being a value calculated by subtracting every subsequent sample from a sample that is y samples ago.

i.e., heart rate change = current heart rate value (*n*) − earlier heart rate value (*n* − *y*)

Thus, the heart rate change may be calculated by subtracting sets of two subsequent heart rates.

At block 725, a subsequent heart rate of heart 8 may be measured. This may be, for example, an automatic or routine measurement. For example, IMD 10 may monitor the heart rate of heart 8 in a manner described above. Alternatively, this may be a value measured by the physician or under previously determined conditions set by the set by a physician, selected from a look-up table or database, or calculated (e.g., the measurement taken at block 725 may be taken once every day or before exercise.).

The value measured at block 725 may provide another heart rate value for comparison to the value found at blocks 710 or 715. This too, may be, for example, an automatic or routine measurement. For example, IMD 10 may monitor the heart rate of heart 8 in a manner described above. Alternatively, this may be a value measured by the physician or under previously determined conditions set by the set by a physician, selected from a look-up table or database, or calculated (e.g., the measurement taken at block 725 may be taken once every day or after exercise).

At block 730 previously stored or previously determined heart rate-change values are adapted and/or updated based on data gathered in the preceding steps. These heart rate-change values may be, for example, average heart rate-change, maximum heart-rate change, and minimum heart-rate change (both positive and negative changes).

At block 732, the updated values from block 730 are subsequently stored in specific time slots, resulting in an overview of these values over time, with each time slot having its own stored values (average, maximum, minimum etc.)

At block 745, the change between the value determined at block 730 and that determined at block 725 may be evaluated against the values stored at block 732 or against other previously stored and/or predetermined values, for example previous average/maximum/minimum values set by the physician or stored in lookup tables or databases. If the change is significant, the method may proceed to block 750. The significance of the change may be determined under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

A significant change may be, for example, one which exceeds a predetermined value, for example, the baseline value determined above, a value set by a physician, selected from a look-up table or database, or otherwise calculated.

For example, a significant change may be heart rate-change values that are higher than standard values or that are lower than standard values. As shown at block 750, a significant change such as this may indicate possible heart failure. If possible heart failure is indicated, several optional steps may be taken including those indicated at blocks 752, 757. For example, the patient and/or physician may be warned by any suitable means such as, for example, an audible alert from IMD 10, a visual indication such as on an external monitor. In some embodiments of the invention, therapy may be administered, for example, by the physician or by IMD 10. In some embodiments of the invention, the therapy administered is one or more appropriate pacing therapies. If the value drops more than a certain value, a warning can be given (in addition to showing the trend of the values over time). Also here several levels of warning could be established for different values of change.

Additionally, some embodiments of the invention provide for the storage of one or more of the values determined in accordance with the present invention. For example, optional steps indicated at 712, 722, and 732 show the storage of initial heart rate values 620, 630, baseline heart rate change value 640, other heart rate values 635, other heart rate change value 645. These values may be used to determine individualized trends of heart 8 over time or may be used in other suitable calculations including, but not limited, predetermining baseline heart rate change values.

If the change is not significant, the method may return to blocks 710, 715 and/or 725 and measure additional heart rate change values in accordance with the present invention.

Figure 8:
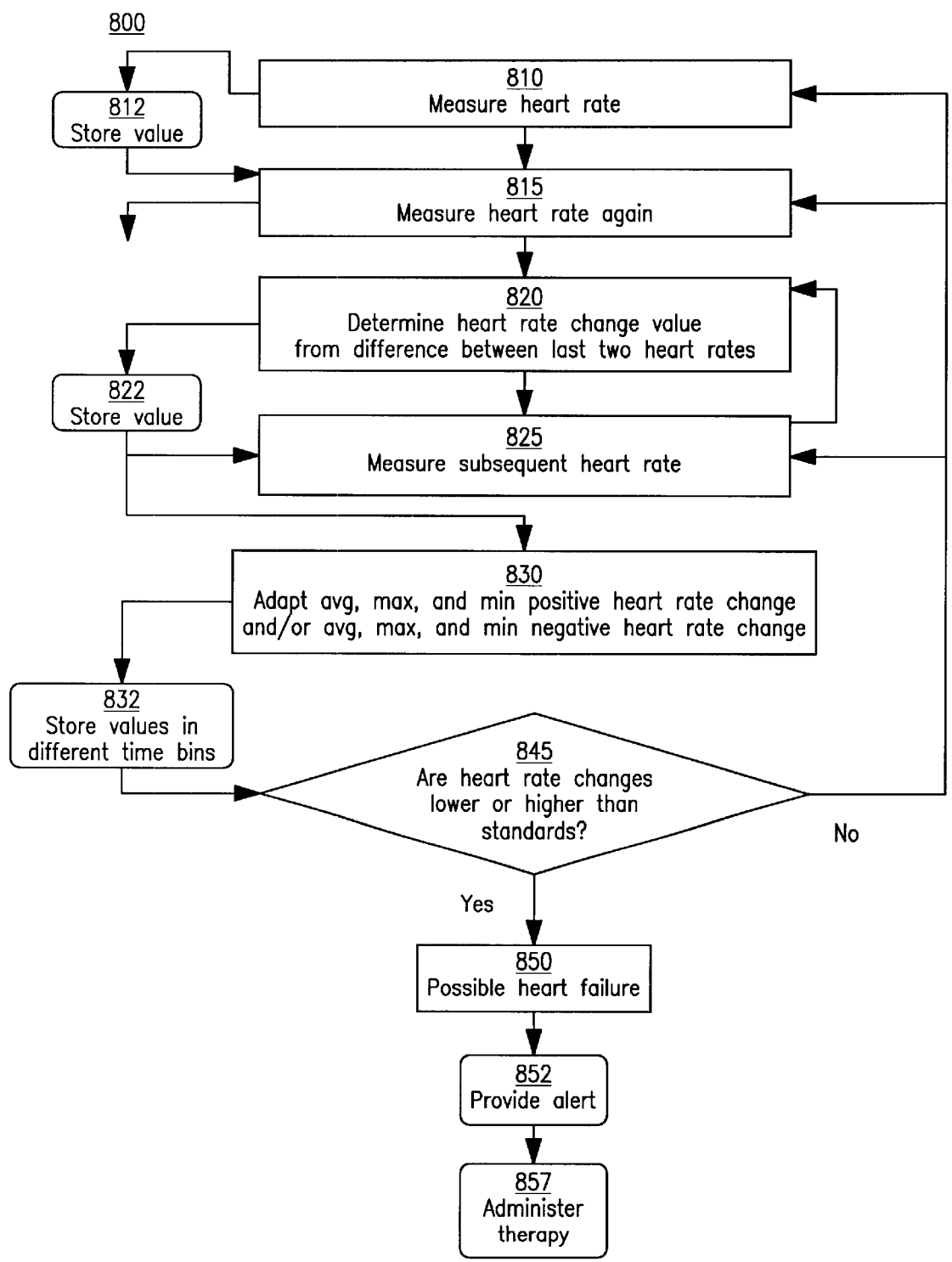
FIG. 8 is a flow diagram of one embodiment of a method for monitoring heart rate changes in accordance with the present invention.

FIG. 8 illustrates one embodiment of a method for monitoring a human heart in accordance with the teachings of the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

At block 810 a measurement of initial heart rate 620 is determined in accordance with one or more of the methods of determining same described above. Alternatively, initial heart rate 620 may be set by a physician, selected from a look-up table or database, or calculated.

At block 815, another initial heart rate measurement is taken after a predetermined time. This predetermined time may be a time set or selected automatically by a physician. The time may range anywhere between the entirety of time period 600 and some portion or fraction thereof. The heart rate measurement may also be taken after certain predetermined conditions are met, for example, after stress to the heart or after exercise.

At block 820, a baseline heart rate change 610 is determined. This heart rate change may be, for example, the change in heart rate from the first measurement of initial heart rate to the second measurement of initial heart rate. The heart rate change value may be expressed in any suitable manner, for example, as a function over time, e.g., a 25 bpm change over 40 minutes, as a constant, e.g. a 0.625 heart rate change value, or as a percentage, a 62.5% change in heart rate. In one embodiment of the invention, different measurements may be taken by sampling every x seconds with the resulting heart rate-change being a value calculated by subtracting every subsequent sample from the previous one i.e., heart rate change = current heart rate value ($n$) − previous heart rate value ($n-1$)

where n represents a sample number.

Alternatively, different measurements may be taken by sampling every x seconds with the resulting heart rate-change with the resulting heart rate-change being a value calculated by subtracting every subsequent sample from a sample that is y samples ago.

i.e., heart rate change = current heart rate value ($n$) − earlier heart rate value ($n-y$)

Thus, the heart rate change may be calculated by subtracting sets of two subsequent heart rates.

At block 825, a subsequent heart rate of heart 8 may be measured. This may be, for example, an automatic or routine measurement. For example, IMD 10 may monitor the heart rate of heart 8 in a manner described above. Alternatively, this may be a value measured by the physician or under previously determined conditions set by the set by a physician, selected from a look-up table or database, or calculated (e.g., the measurement taken at block 725 may be taken once every day or before exercise.)

The value measured at block 825 may provide another heart rate value for comparison to the value found at blocks 710 or 715. This too, may be, for example, an automatic or routine measurement. For example, IMD 10 may monitor the heart rate of heart 8 in a manner described above. Alternatively, this may be a value measured by the physician or under previously determined conditions set by the set by a physician, selected from a look-up table or database, or calculated (e.g., the measurement taken at block 825 may be taken once every day or after exercise.)

At block 830 previously stored or previously determined heart rate-change values are adapted and/or updated based on data gathered in the preceding steps. These heart rate-change values may be, for example, average heart rate-change, maximum heart-rate change, and minimum heart-rate change (both positive and negative changes).

At block 832, the updated values from block 830 are subsequently stored in specific time slots, resulting in an overview of these values over time, with each time slot having its own stored values (average, maximum, minimum etc.).

At block 845, the change between the value determined at block 830 and that determined at block 825 may be evaluated against the values stored at block 832 or against other previously stored and/or predetermined values, for example previous average/maximum/minimum values set by the physician or stored in lookup tables or databases. If the change is significant, the method may proceed to block 850. The significance of the change may be determined under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

A significant change may be, for example, one which exceeds a predetermined value, for example, the baseline value determined above, a value set by a physician, selected from a look-up table or database, or otherwise calculated.

For example, a significant change may be indicated over time, as indicated at block 860. For example, if the heart rate changes are decreasing over time, possible heart failure may be indicated as shown at block 850. If possible heart failure is indicated, several optional steps may be taken including those indicated at blocks 852, 857. For example, the patient and/or physician may be warned by any suitable means such as, for example, an audible alert from IMD 10, a visual indication such as on an external monitor. In some embodiments of the invention, therapy may be administered, for example, by the physician or by IMD 10. In some embodiments of the invention, the therapy administered is one or more appropriate pacing therapies. If the value drops more than a certain value, a warning can be given (in addition to showing the trend of the values over time). Also here several levels of warning could be established for different values of change.

Additionally, some embodiments of the invention provide for the storage of one or more of the values determined in accordance with the present invention. For example, optional steps indicated at 812, 822, and 832 show the storage of initial heart rate values 620, 630, baseline heart rate change value 640, other heart rate values 635, other heart rate change value 645. These values may be used to determine individualized trends of heart 8 over time or may be used in other suitable calculations including, but not limited, predetermining baseline heart rate change values.

If the change is not significant, the method may return to blocks 810, 815 and/or 825 and measure additional heart rate change values in accordance with the present invention.

In the embodiment of the invention seen in FIGS. 7 and 8, the parameters determined include: initial heart rate values, baseline heart rate change values, other heart rate values, other heart rate change values, possible heart failure indicator values and heart rate change comparison values. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the increase of pacing parameters, per se, but may find further application as a measuring means. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method of monitoring heart failure, comprising:
   measuring a first initial heart rate;
   measuring a second initial heart rate;
   determining a baseline heart rate change value that comprises a speed at which the first initial heart rate changes to the second initial heart rate;
   determining at least one subsequent heart rate change value that comprises a subsequent speed at which a first subsequent heart rate changes to a second subsequent heart rate; and
   comparing the subsequent heart rate change value to the baseline heart rate change value to obtain at least one heart failure value.

2. The method of claim 1 wherein the first subsequent heart rate is the same as the first initial heart rate.

3. The method of claim 1 wherein the first subsequent heart rate is the same as the second initial heart rate.

4. The method of claim 1, further comprising:
   measuring a first subsequent heart rate.

5. The method of claim 1, further comprising:
   measuring a second subsequent heart rate.

6. The method of claim 1, further comprising:
   indicating a potential heart failure with the heart failure value when the subsequent heart rate change value is higher than the baseline heart rate change value.

7. The method of claim 1, further comprising:
   indicating a potential heart failure with the heart failure value when the subsequent heart rate change value is lower than the baseline heart rate change value.

8. The method of claim 1, further comprising:
   storing the baseline heart rate change value.

9. The method of claim 1, further comprising:
   storing the subsequent heart rate change value.

10. The method of claim 1, further comprising:
    storing the heart failure value.

11. The method of claim 1, further comprising:
    determining at least one significant heart failure value.

12. The method of claim 11, further comprising:
    indicating a potential heart failure with the heart failure value when the heart failure value matches the significant heart failure value.

13. The method of claim 12 further comprising:
    providing an alert of the potential heart failure.

14. The method of claim 1, further comprising:
    administering therapy based on the heart failure value.

15. The method of claim 1, further comprising:
    pacing at the first initial heart rate.

16. The method of claim 1 further comprising:
    determining an average heart rate change value from the baseline heart rate change and a plurality of subsequent heart rate changes.

17. The method of claim 1 further comprising:
    determining a maximum heart rate change value from the baseline heart rate change and a plurality of subsequent heart rate changes.

18. The method of claim 1 further comprising:
    determining a minimum heart rate change value from the baseline heart rate change and a plurality of subsequent heart rate changes.

19. An implantable medical device, comprising:
    a processor;
    at least one sensing circuit operably connected to the processor;
    at least one sensing electrode operably connected to the processor and adapted for placement within a heart wherein
- a first initial heart rate and a second initial heart rate are measured, a baseline heart rate change value is determined for a speed at which the first initial heart rate changes to the second initial heart rate, a subsequent heart rate change value is determined for a subsequent speed at which a first subsequent heart rate changes to a second subsequent heart rate and the subsequent heart rate change value is compared to the baseline heart rate change value to obtain at least one heart failure value.

20. The device of claim 19 further comprising:
at least one pacing electrode.

21. The device of claim 19 further comprising:
a memory location operably connected to the processor for storing the baseline heart rate change value.

22. The device of claim 19 further comprising:
a memory location operably connected to the processor for storing a subsequent heart rate change value.

23. The device of claim 19 further comprising:
a memory location operably connected to the processor for storing the heart failure value.

24. The device of claim 19 further comprising:
an alert operably connected to the processor for providing an alert when the heart failure value indicates potential heart failure.

25. The device of claim 19 further comprising:
at least one pacing electrode operably connected to the process for administering therapy based on the heart failure value.

26. The device of claim 19 further comprising:
a memory location operably connected to the processor for storing an average heart rate change value.

27. The device of claim 19 further comprising:
a memory location operably connected to the processor for storing a maximum heart rate change value.

28. The device of claim 19 further comprising:
a memory location operably connected to the processor for storing a minimum heart rate change value.

29. An implantable medical system, comprising:
means for measuring a first initial heart rate;
means for measuring a second initial heart rate;
means for determining a baseline heart rate change value that comprises a speed at which the first initial heart rate changes to the second initial heart rate;
means for determining at least one subsequent heart rate change value that comprises a subsequent speed at which a first subsequent heart rate changes to a second subsequent heart rate; and
means for comparing the subsequent heart rate change value to the baseline heart rate change value to obtain at least one heart failure value.

30. The system of claim 29, further comprising:
means for pacing at the first initial heart rate.

31. The system of claim 29, further comprising:
computer program code that paces at the first initial heart rate.

32. A computer usable medium including a program for monitoring heart failure, comprising:
computer program code that measures a first initial heart rate;
computer program code that measures a second initial heart rate;
computer program code that determines a baseline heart rate change value that comprises a speed at which the first initial heart rate changes to the second initial heart rate;
computer program code that determines at least one subsequent heart rate change value that comprises a subsequent speed at which a first subsequent heart rate changes to a second subsequent heart rate; and
computer program code that compares the subsequent heart rate change value to the baseline heart rate change value to obtain at least one heart failure value.

33. The program of claim 32, further comprising:
means for measuring a first subsequent heart rate.

34. The program of claim 32, further comprising:
means for measuring a second subsequent heart rate.

35. The program of claim 32, further comprising:
means for indicating a potential heart failure with the heart failure value when the subsequent heart rate change value is higher than the baseline heart rate change value.

36. The program of claim 32, further comprising:
means for indicating a potential heart failure with the heart failure value when the subsequent heart rate change value is lower than the baseline heart rate change value.

37. The program of claim 32, further comprising:
means for storing the baseline heart rate change value.

38. The program of claim 32, further comprising:
means for storing the subsequent heart rate change value.

39. The program of claim 32, further comprising:
means for storing the heart failure value.

40. The program of claim 32, further comprising:
means for determining at least one significant heart failure value.

41. The system of claim 40, further comprising:
means for indicating a potential heart failure with the heart failure value when the heart failure value matches the significant heart failure value.

42. The system of claim 41 further comprising:
means for providing an alert of the potential heart failure.

43. The program of claim 32, further comprising:
means for administering therapy based on the heart failure value.

44. The program of claim 32 further comprising:
means for determining an average heart rate change value from the baseline heart rate change and a plurality of subsequent heart rate changes.

45. The program of claim 32 further comprising:
means for determining a maximum heart rate change value from the baseline heart rate change and a plurality of subsequent heart rate changes.

46. The program of claim 32 further comprising:
means for determining a minimum heart rate change value from the baseline heart rate change and a plurality of subsequent heart rate changes.

47. The program of claim 32, further comprising:
computer program code that measures a first subsequent heart rate.

48. The program of claim 32, further comprising:
computer program code that measures a second subsequent heart rate.

49. The program of claim 32, further comprising:
computer program code that indicates a potential heart failure with the heart failure value when the subsequent heart rate change value is higher than the baseline heart rate change value.

50. The program of claim 32, further comprising:

computer program code that indicates a potential heart failure with the heart failure value when the subsequent heart rate change value is lower than the baseline heart rate change value.

51. The program of claim 32, further comprising:

computer program code that stores the baseline heart rate change value.

52. The program of claim 32, further comprising:

computer program code that stores the subsequent heart rate change value.

53. The program of claim 32, further comprising:

computer program code that stores the heart failure value.

54. The program of claim 32, further comprising:

computer program code that determines at least one significant heart failure value.

55. The program of claim 54, further comprising:

computer program code that indicates a potential heart failure with the heart failure value when the heart failure value matches the significant heart failure value.

56. The program of claim 55 further comprising:

computer program code that provides an alert of the potential heart failure.

57. The program of claim 32, further comprising:

computer program code that administers therapy based on the heart failure value.

58. The program of claim 32 further comprising:

computer program code that determines an average heart rate change value from the baseline heart rate change and a plurality of subsequent heart rate changes.

59. The program of claim 32 further comprising:

computer program code that determines a maximum heart rate change value from the baseline heart rate change and a plurality of subsequent heart rate changes.

60. The program of claim 32 further comprising:

computer program code that determines a minimum heart rate change value from the baseline heart rate change and a plurality of subsequent heart rate changes.

\* \* \* \* \*